(12) United States Patent
Cote

(10) Patent No.: US 7,055,248 B2
(45) Date of Patent: Jun. 6, 2006

(54) SURGICAL KNIFE BLADE ATTACHMENT AND METHOD FOR USING SAME

(75) Inventor: Dana M. Cote, Saugus, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/835,286

(22) Filed: Apr. 30, 2004

(65) Prior Publication Data
US 2005/0245953 A1 Nov. 3, 2005

(51) Int. Cl.
B26B 5/00 (2006.01)

(52) U.S. Cl. .................... 30/337; 30/339; 606/167; 606/176

(58) Field of Classification Search ............. 30/337, 30/339; 606/167, 176, 177, 178, 180
See application file for complete search history.

(56) References Cited

U.S. PATENT DOCUMENTS

| | | | |
|---|---|---|---|
| 3,383,763 A * | 5/1968 | Strandfors | 30/339 |
| 4,660,287 A | 4/1987 | Decker | 30/339 |
| 5,203,865 A | 4/1993 | Siepser | 606/166 |
| 5,336,235 A | 8/1994 | Myers | 606/166 |
| 5,344,424 A * | 9/1994 | Roberts et al. | 606/167 |
| 5,433,321 A | 7/1995 | Abidin et al. | 206/354 |
| 5,475,925 A * | 12/1995 | Newman et al. | 30/339 |
| 5,507,762 A | 4/1996 | Abidin et al. | 606/167 |
| 5,528,811 A | 6/1996 | Abidin et al. | 29/428 |
| 5,924,206 A | 7/1999 | Cote et al. | 30/337 |
| 6,112,420 A * | 9/2000 | Schickerling | 30/392 |
| 6,626,925 B1 * | 9/2003 | Newman et al. | 606/167 |
| 6,629,985 B1 * | 10/2003 | Kiehne | 30/339 |
| 6,854,187 B1 * | 2/2005 | Huan | 30/339 |
| 2002/0065532 A1 | 5/2002 | Harrold et al. | 606/166 |
| 2002/0143352 A1 * | 10/2002 | Newman et al. | 606/167 |
| 2004/0215174 A1 | 10/2004 | Morawski et al. | 606/4 |

FOREIGN PATENT DOCUMENTS

WO   WO 01/05312 A1 * 1/2001 ............... 30/339

* cited by examiner

Primary Examiner—Timothy V. Eley
Assistant Examiner—Jason Prone
(74) Attorney, Agent, or Firm—Roylance, Abrams, Berdo & Goodman, LLP

(57) ABSTRACT

A system and method are disclosed for securing a blade to a blade post or handle base. A handle base is provided with a receiving port that includes a taper or dovetail configuration along a portion of each wall. The receiving port accepts a blade, and a cap is positioned within the exposed receiving port above the blade surface. The sides of the cap are secured within the dovetail sections along each wall of the receiving port and opposite securing ramps engage to secure the blade into position. The blade may be a keratome blade that is intended for opthalmic use, but the system and method can be used in connection with various types of opthalmic and non-opthalmic surgical knives.

7 Claims, 15 Drawing Sheets

SURGICAL KNIFE BLADE ATTACHMENT AND METHOD FOR USING SAME

FIELD OF THE INVENTION

The present invention relates to a system and method for securely attaching a blade to a surgical knife handle for both ophthalmic and non-ophthalmic applications.

BACKGROUND OF THE INVENTION

In various surgical procedures, the physician typically has to make an incision in the patient in order to remove unwanted tissue, repair damaged tissue, implant a device, or perform exploratory surgery, among other procedures, to improve the patient's well being. In certain cases, two or more of these activities must be done in a single procedure. For example, in cataract surgery the physician removes the natural lens that has been clouded by a cataract from the patient's eye and replaces it with an artificial lens that will improve the patient's eyesight. In order to perform this procedure, an incision is made in the cornea of the eye by the physician using a scalpel. This provides the physician with access to the patient's lens whereby the clouded lens is cut loose and removed. As known to those skilled in the art, there are a number of different procedures such as extra-capsular surgery and phacoemulsification that are used to remove a patient's lens that has a cataract, and still further, a number of devices for use in these procedures.

Typically a nurse or other surgical assistant manages the devices that are used during such intricate surgeries. For example, the assistant ensures that the appropriate sterile devices are available in the operating suite for the particular procedure that is to be performed. With respect to scalpels, the nurse often hands the scalpel to the physician in a predetermined orientation so that the physician can grip the scalpel's handle without taking his or her eyes away from the patient. This also minimizes the possibility that the physician will be cut with the blade on the scalpel. After the physician completes the incision, the scalpel is handed back to the assistant for proper disposal or sterilization. This requires the assistant to place the used scalpel on a particular tray that will be removed after the procedure is completed. The devices on the tray are then disposed of, or are sterilized for reuse.

Examples of such prepared devices include keratome blades that are used for cutting eye tissue and which are commonly provided in sterile packaging. Details of keratome blade devices are discussed in U.S. Patent Application Publication No. U.S. 2002/0065532 issued to Harrold et al., the entire content of which is incorporated herein by reference. As noted in the Harrold patent application, when a keratome blade is to be inserted into a keratome, a package is opened and the keratome blade is grasped by a user with gloved or otherwise covered fingers. Often the blade is first inspected under a microscope to ensure that the cutting edge of the blade is intact. Such inspections, however, may be difficult to perform with tweezers or finger grasping since, in either case, the user must exert a force to hold the blade, and while held, portions of the blade will be hidden from view by the holder. After inspection, the blade is manually placed onto a blade support that is inserted into a keratome. During this process, there is a possibility that contaminants or particulates can be introduced to the blade or the cutting edge may be damaged. Furthermore, in handling the blade with fingers, the user faces a risk of being cut by the blade even when the use precautions noted above are followed.

Accordingly, a need exists for a system and method for securely attaching a blade to a surgical knife handle, and allowing manipulation and inspection, while eliminating the risks and difficulties described above.

SUMMARY OF THE INVENTION

It is therefore an object of this invention to provide a system and method which can be used to securely attach a blade to a handle, which allows a broad range of use with minimal risks to the blade or blade user.

It is another object of this invention to provide a system and method which provides a handle base which can receive and position a blade and, thereafter, receive a cap to secure the blade to the handle base.

It is another object of the invention to provide a system and method which secures a blade to a handle base using a dovetail connection between a cap and a receiving port in the handle base.

It is another object of the invention to provide a system and method which secures a cap in a dovetail connection using a snap action between inclined ramps on the cap and a receiving port.

It is another object of the invention to provide a system and method in which a secured blade and cap are flush with the surface of the handle base.

These and other objects are substantially achieved by providing a system and method for a blade support, blade and blade support cap, that includes a handle base with a receiving port. The receiving port is generally circular about a center securing ramp and includes a taper or dovetail configuration along a portion of the receiving port walls. The receiving port accepts a blade, such as a keratome blade, that includes an opening through which the center securing ramp protrudes when the blade is in position. A cap is positioned and secured above the blade within the dovetail sections along the walls of the receiving port. A second securing ramp, located on a lower surface of the cap, engages the center securing ramp of the port and locks the cap in place within the dovetail connection and secures the blade into position.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numerals refer to like elements and in which.

In the drawing figures, it will be understood that like numerals refer to like structures.

DETAILED DESCRIPTION OF THE PREFERRED EMBODIMENTS

The embodiment of the present invention described below discloses a system and method to secure a blade to a blade post or handle base, such as a keratome blade found at the distal end of a surgical knife for both ophthalmic and non-ophthalmic applications. The system and method includes a handle base with a receiving port, described in greater detail below, that is generally circular about a center securing ramp and includes a taper, or dovetail configuration, along a portion of one or more receiving port walls.

The receiving port accepts a blade such as a keratome blade that includes an opening through which the center securing ramp protrudes when the blade is in position within the receiving port. A cap, which has a shape substantially similar to the receiving port shape, is positioned within the exposed receiving port and above the blade surface such that the tapered sides of the cap are secured within the dovetail sections along each wall of the receiving port. As the cap is positioned, a second securing ramp located on a lower surface of the cap engages with the center securing ramp of the port and serves to lock the cap in place and secures the blade in position.

Figure 1:
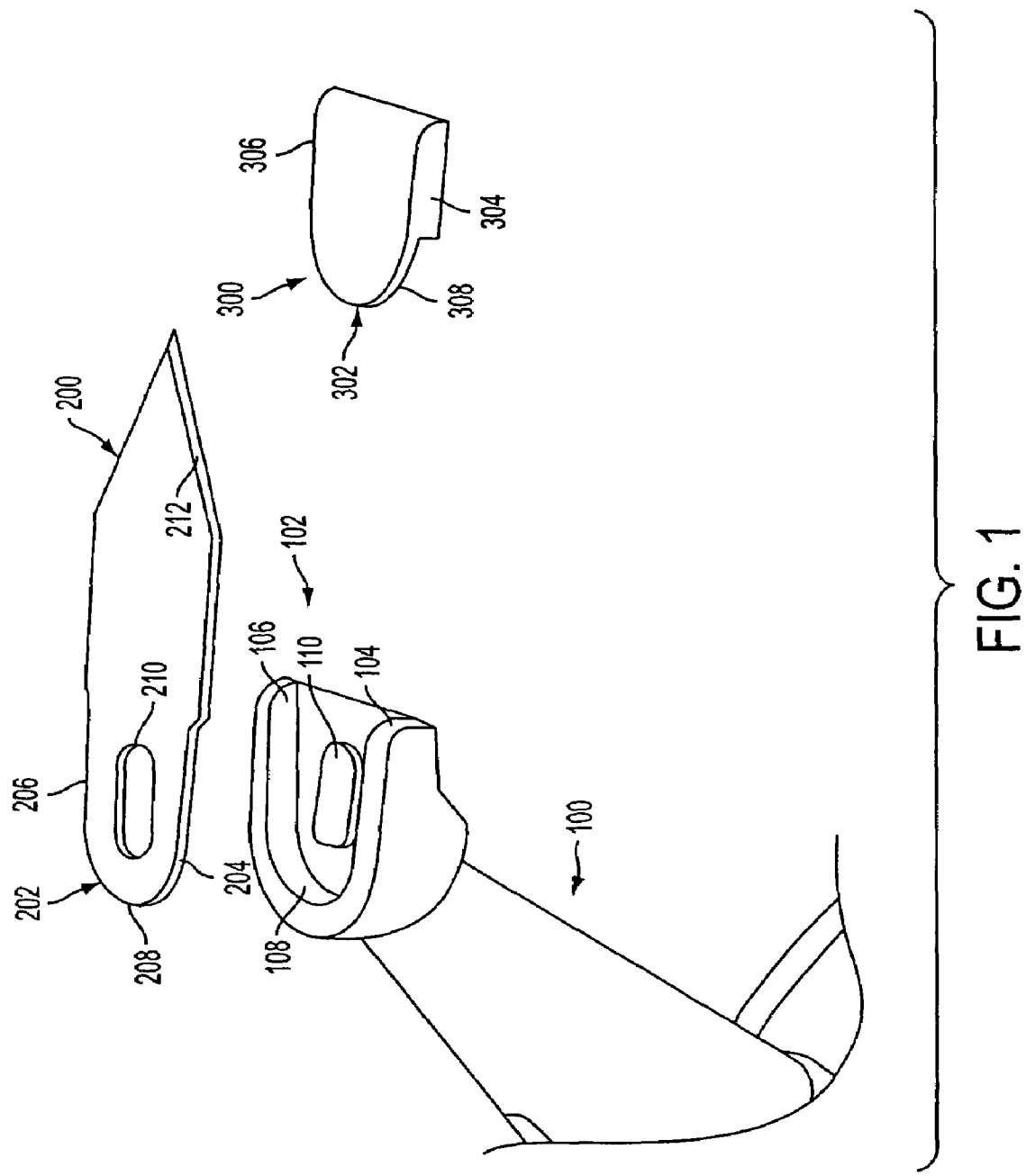
FIG. 1 is an exploded perspective view of an embodiment of the present invention.

As shown in FIG. 1, the system and method of the preferred embodiment includes a handle base 100, a blade 200, and a cap 300. FIG. 1 is an enlarged exploded view of an embodiment of the present invention. As shown in FIG. 1, the handle base 100 includes a receiving port 102 having a first and second dovetailed port side 104 and 106, respectively. The handle base also includes a circular port side 108, and a center securing ramp 110. The receiving port 102 of the handle base 100 receives a blade such as blade 200, which is then secured with a cap 300.

Figure 2:
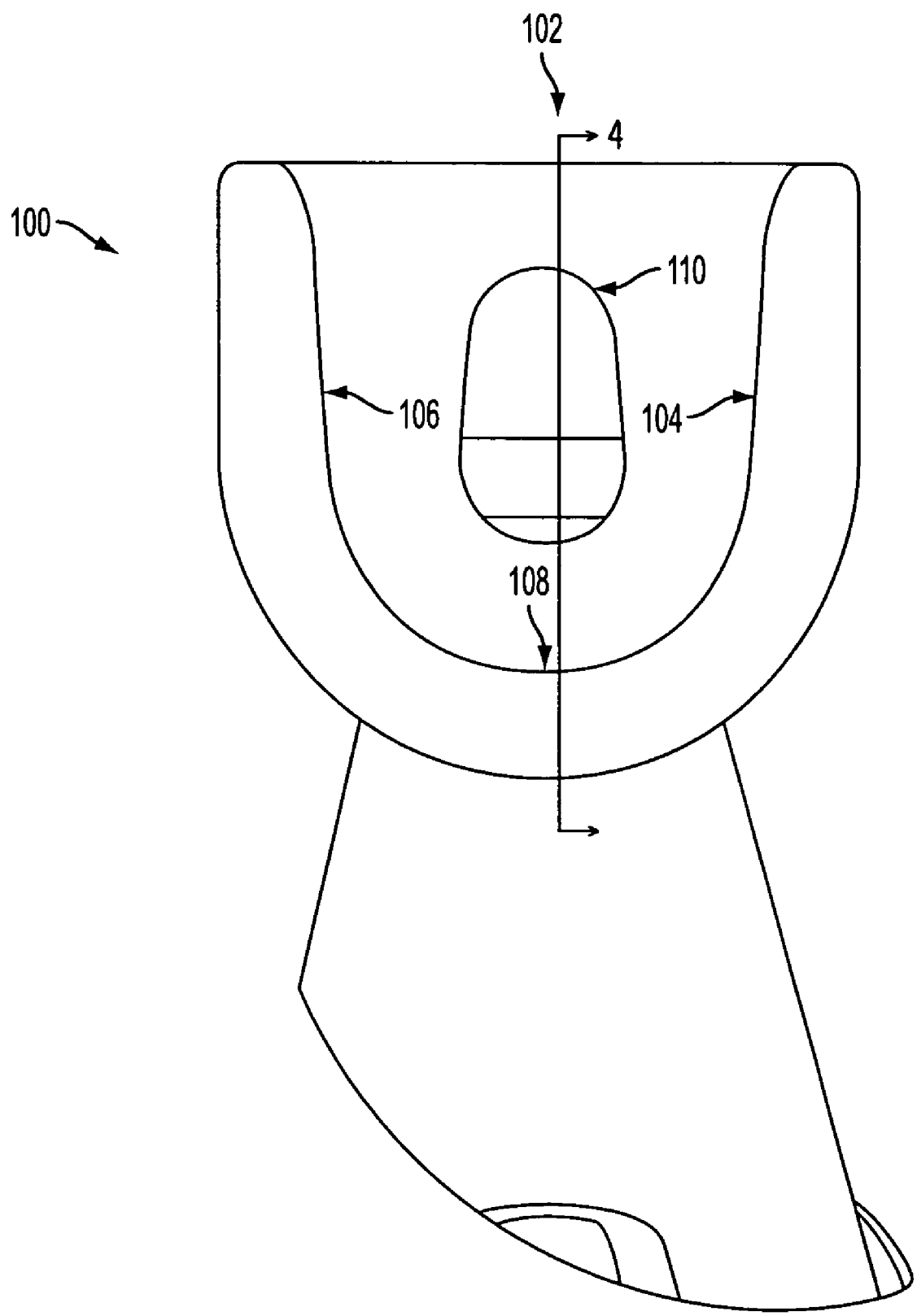
FIG. 2 is a top view of the handle base of FIG. 1.
Figure 3:
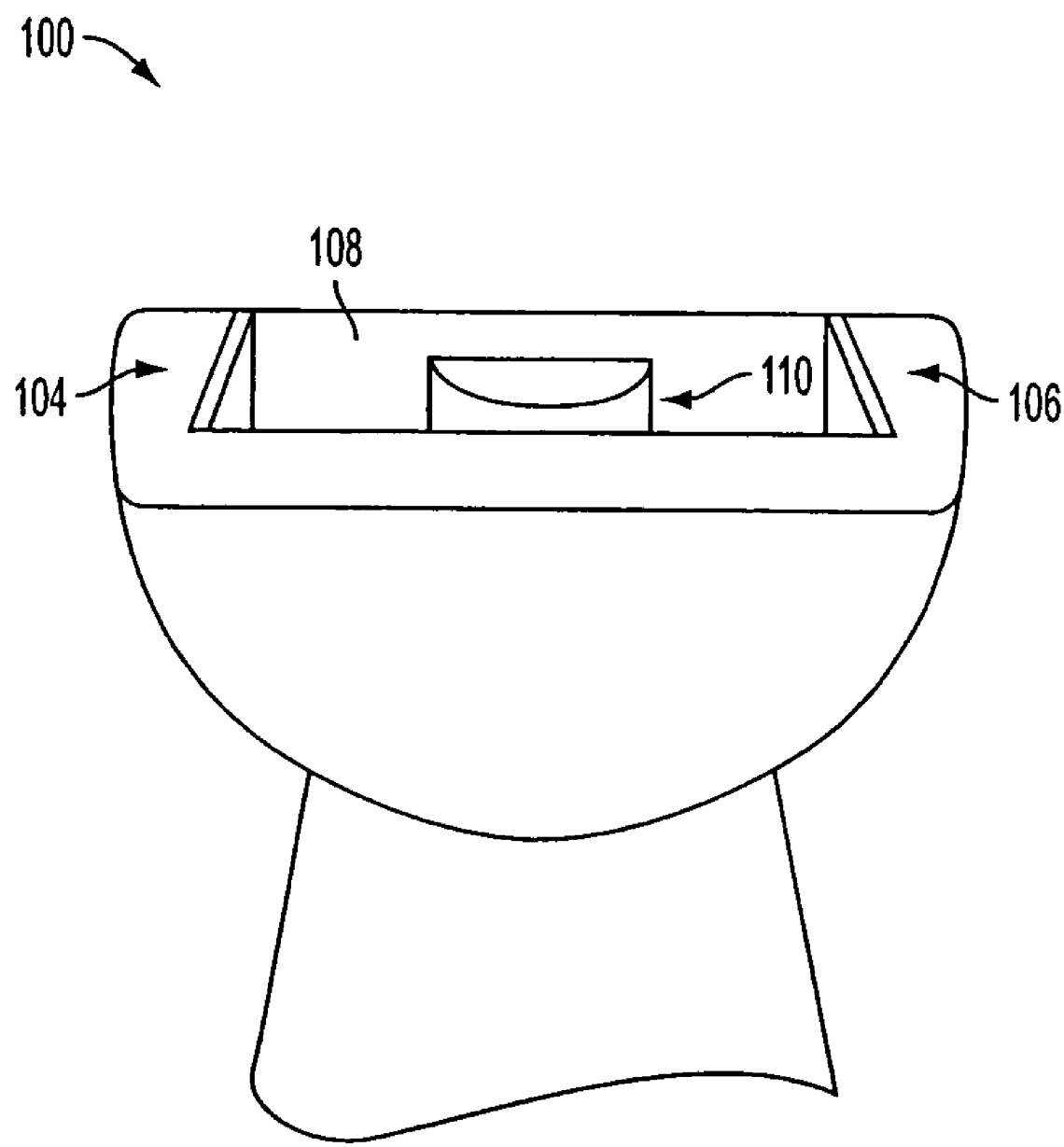
FIG. 3 is a front elevational view of the handle base of FIG. 1.
Figure 4:
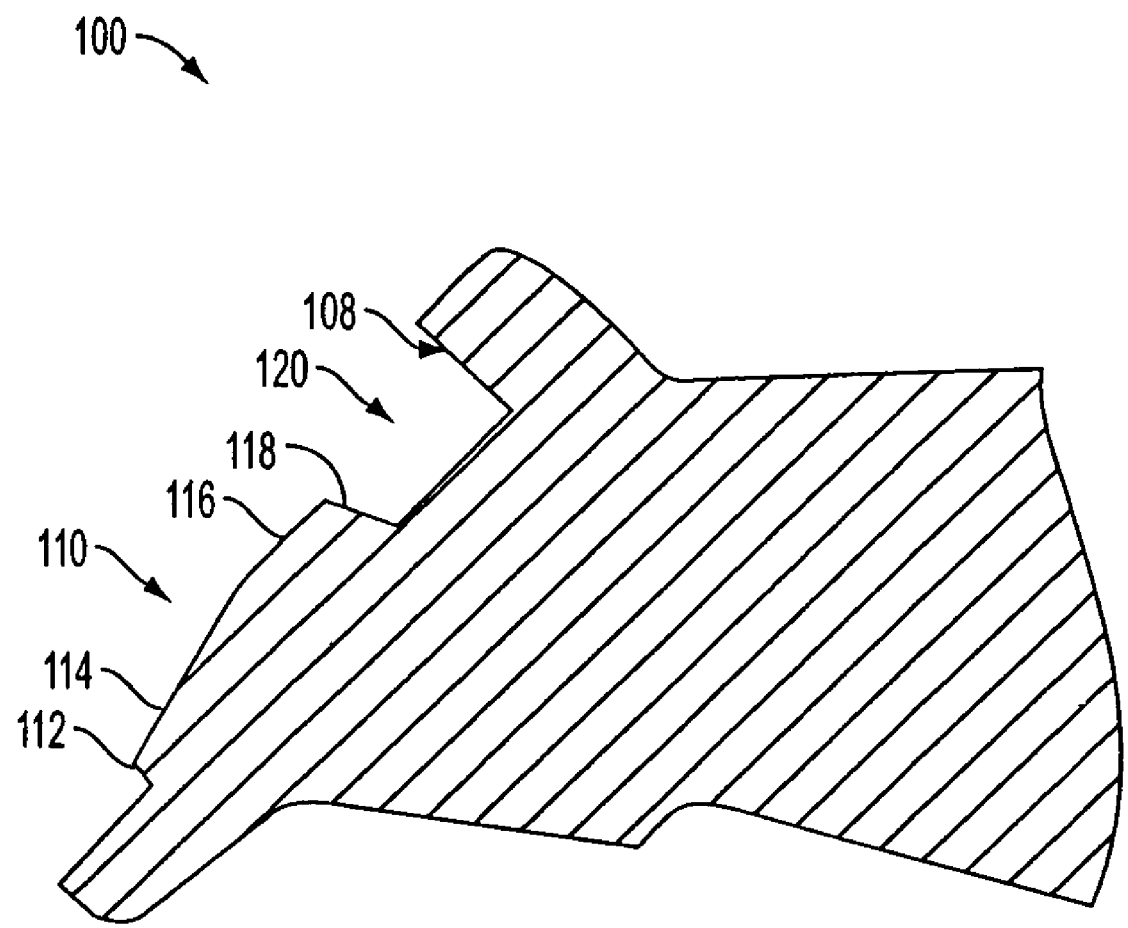
FIG. 4 is a cross-sectional view (4—4 in FIG. 2) of the handle base of FIG. 1.

The handle base 100 is shown in greater detail in FIGS. 2, 3, and 4. FIGS. 2 and 3 are enlarged top and front views, respectively, of a handle base as shown in FIG. 1. FIG. 4 is an enlarged cross-sectional view (4—4 in FIG. 2) of a handle base as shown in FIG. 1.

As shown in greater detail in FIG. 2, the handle base 100 includes a receiving port 102 bounded on three sides by tapered, or dovetailed, port sides 104 and 106, and a circular port side 108. Within the receiving port 102, a center securing ramp 110 is also positioned. In FIG. 3, the front elevational view of the handle base shows the dovetailed port sides 104 and 106 of the receiving port 102 in greater detail. As shown in FIG. 3, each side 104 and 106 is designed to slidably engage with a corresponding and similarly tapered side of a cap 300 that is described in greater detail below.

Each of the sides 104 and 106 extend from the surface of the receiving port 102 at an angle. The sides can be constructed at any number of angles, including acute angles sufficient to create a taper or dovetailed port opening. The angle can also be chosen to prevent the cap 300 from being easily displaced in a perpendicular direction from the receiving port 102 of the handle base 100. In the example shown in FIG. 3, sides 104 and 106 extend from the surface of the receiving port 102 at an angle of approximately 20 degrees. The taper of each side 104 and 106 is one of several techniques used to secure the cap 300 to the handle base 100. A second technique to prevent the cap 300 from being easily displaced in a parallel direction from the receiving port 102 is the center securing ramp 110.

In FIG. 4, the center securing ramp 110 is shown in greater detail. The center securing ramp 110 includes a rounded end 112 at a height slightly less than a raised flat end 116. The height of the securing ramp 110 at the rounded end 112 is equal to or slightly less than the thickness of the blade 200 (not shown), allowing easier engagement with the cap 300 once the blade is in position as described in greater detail below. The reduced height results from an incline between the rounded end 112 and the raised flat end 116. This incline 114 is used to engage a second securing ramp (shown at 310 in FIG. 5) on the cap 300. The incline 114 assists in slightly displacing the second securing ramp 310 of the cap in a perpendicular direction from the receiving port 102 against the restriction provided by the tapered sides described above, and over the raised flat end 116. As the second securing ramp 310 passes the raised flat end 116, it snaps to an original position and lodges within the opening 120 behind the center securing ramp 110. The rear surface 118 of the center securing ramp 110 lacks an incline as described above, thereby preventing a reverse motion of the second securing ramp 310 in a parallel direction to the receiving port 102.

Before securing the cap 300, the receiving port 102 of the handle base 100 is configured to receive and secure a blade such as a keratome blade. The engagement between the blade 200 and the handle base 100 substantially occurs by positioning the blade 200 above the receiving port 102 and sliding the blade downward into the port, thereby engaging the elements described in greater detail below.

Returning to FIG. 1, the blade 200 includes a contoured end 202 which has shouldered first and second sides 204 and 206, respectively, and a circular side 208. An opening 210 is provided through which the center securing ramp 110 can securely protrude (e.g., the ramp 110 can be dimensioned for frictional engagement with the inner circumference of the opening 210). The opening 210 and center securing ramp 110 mate during blade placement into the receiving port 102 such that the blade 200 is positioned correctly and blade twisting is prevented.

The correct positioning of the blade 200 is also ensured by the engagement between the shouldered first and second sides 204 and 206 of the blade and the first and second port sides 104 and 106, respectively, of the receiving port 102. The shoulder of each side 204 and 206 of the blade 200 securely presses against the exterior of the receiving port 102 when the opening 210 of the blade and the center securing ramp 110 are mated. This ensures that the blade 200 is firmly held within the receiving port 102 and in a correct position and thereafter, is secured to the base with the cap 300. The blade 200 also includes a sharpened, or functional end 212 which can be configured in any number of ways without restricting the scope of the embodiment of the present invention.

Figure 5:
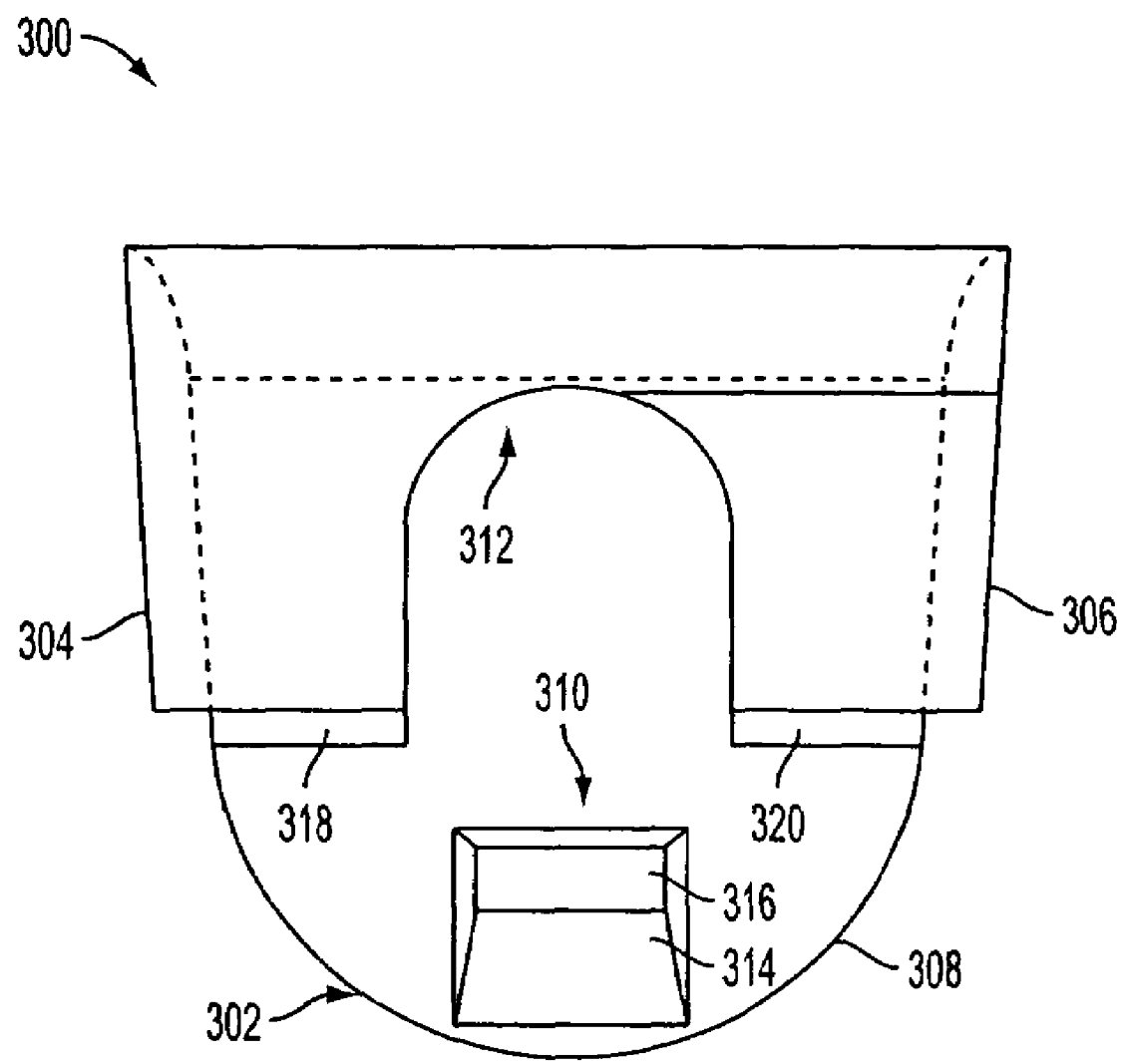
FIG. 5 is a bottom view of the cap of FIG. 1.
Figure 6:
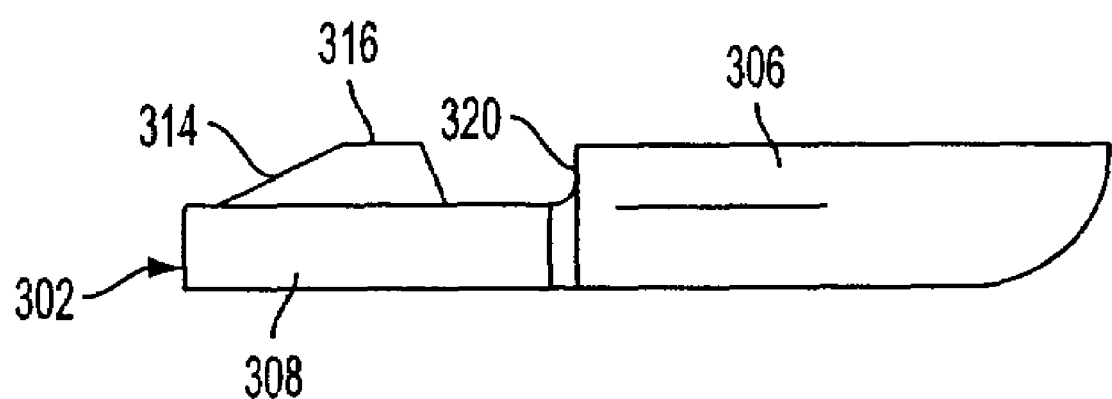
FIG. 6 is a side elevational view of the cap of FIG. 1.

The cap 300 that is used to secure the blade 200 to the handle base 100 is shown in greater detail in FIGS. 5 and 6. FIG. 5 is an enlarged bottom view of a cap as shown in FIG. 1, and FIG. 6 is an enlarged side elevational view of a cap as shown in FIG. 1. The engagement between the cap 300 and the handle base 100 substantially occurs by positioning the cap on the exposed surface of the properly positioned blade 200, and sliding the cap tightly against the blade surface and into the receiving port 102 extending above the blade surface, thereby engaging the elements described in greater detail below.

The cap 300 of FIG. 1 includes a contoured end 302 which has shouldered first and second sides 304 and 306, respectively, and a circular side 308. The cap 300 also includes the second securing ramp 310 which engages the center securing ramp 110 during cap installation. The first and second sides 304 and 306 include a taper which slidably engage with the first and second dovetailed receiving port sides 104 and 106, respectively, during cap installation. As described above, the engagement between sides 104 and 106 of the receiving port and sides 304 and 306 of the cap, respectively, prevents cap movement in a perpendicular direction from the receiving port 102 of the handle base 100.

The cap 300 further includes a shoulder 318 and 320 as shown in greater detail in FIGS. 5 and 6. Beyond this shoulder toward the contoured end 302, the cap thickness is reduced to allow, among other things, easy deflection of the second securing ramp 310 during installation and flush cap mounting after installation. Opposite the contoured end 302, the cap thickness increases at the shoulder 318 and 320 to fill the full depth of the receiving port 102 after installation. As shown in FIG. 5, the cap midsection also includes a relief 312 extending from the shoulders 318 and 320. The relief 312 extends the reduced thickness of the contoured end a slight distance beyond shoulders 318 and 320 to accept the center securing ramp 110 and allow the cap 300 to remain flush within the receiving port 102 after installation.

As shown in greater detail in FIGS. 5 and 6, the cap 300 has a circular side 308 which mates with the circular side 108 of the receiving port 102. Adjacent to the contoured end 302, the cap 300 includes a second securing ramp 310 which includes an incline 314 rising to a flat surface 316. The incline 314, as with the incline 114 of FIG. 4, is used to engage the center securing ramp 110. The engagement between inclines 314 and 114 displaces the second securing ramp 310 slightly upwards against the restriction provided by the slidable engagement between tapered sides 304 and 306, and 104 and 106, respectively. Slightly further in the engagement, the second securing ramp 310 passes over the raised flat end 116 of the center securing ramp 110 and snaps to an engaged position, lodging within the opening 120 behind the center securing ramp 110 as described above. The dovetail sides, 304 and 306, and 104 and 106 respectively, of the cap and handle base, are tapered such that, as the two parts first engage, there is a loose fit. As the cap 300 is slid into its final position, the gap decreases to a slight press-fit. The dovetail tapers in such a press-fit situation operate to pull the major inside surface of the cap 300 down against the blade 200. This ensures that there is no wobble after assembly and that the ramps 110 and 310 snap to keep the parts together.

Figure 7:
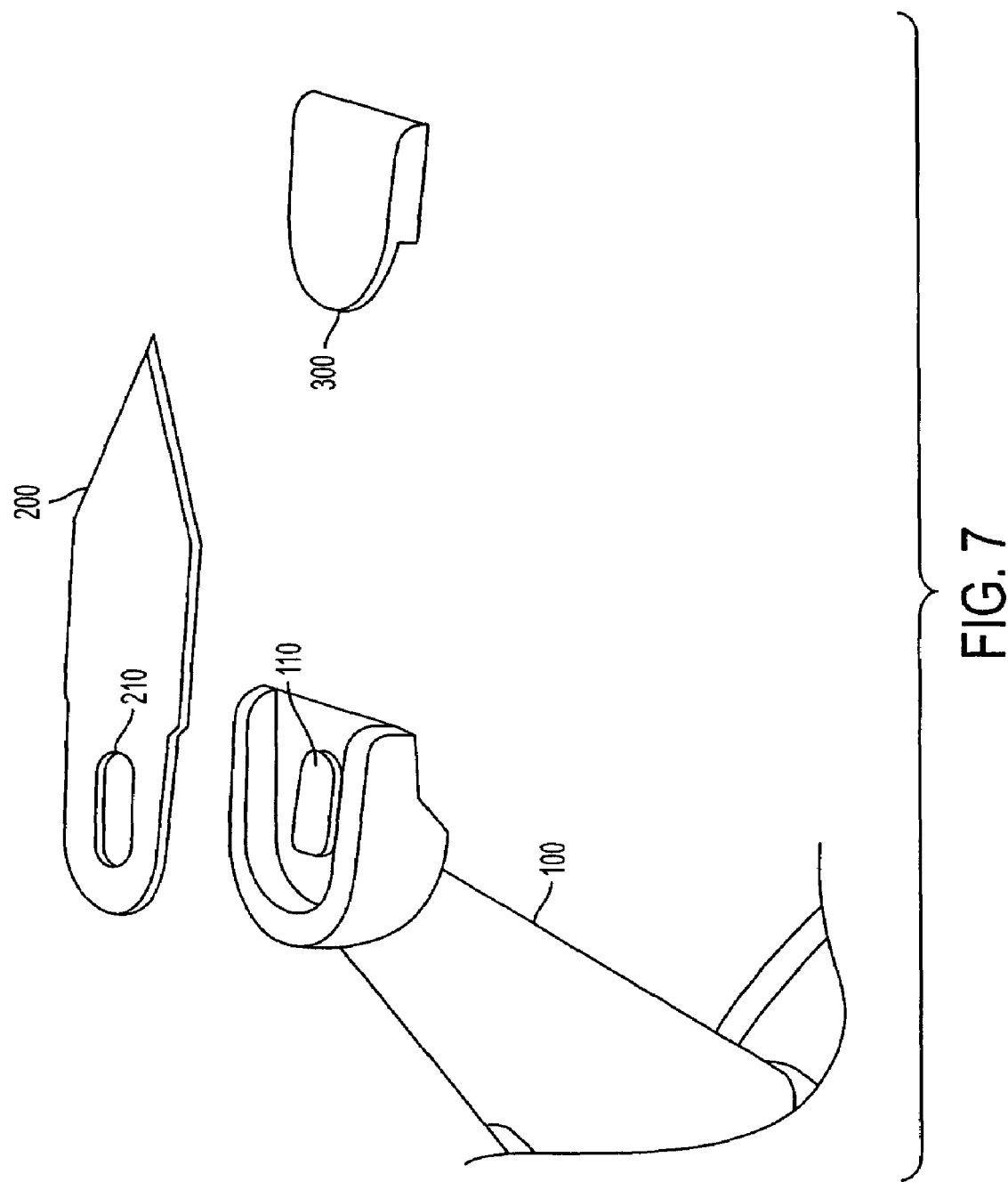
FIG. 7 is an exploded perspective view of the handle base, blade and cap prior to assembly.
Figure 8:
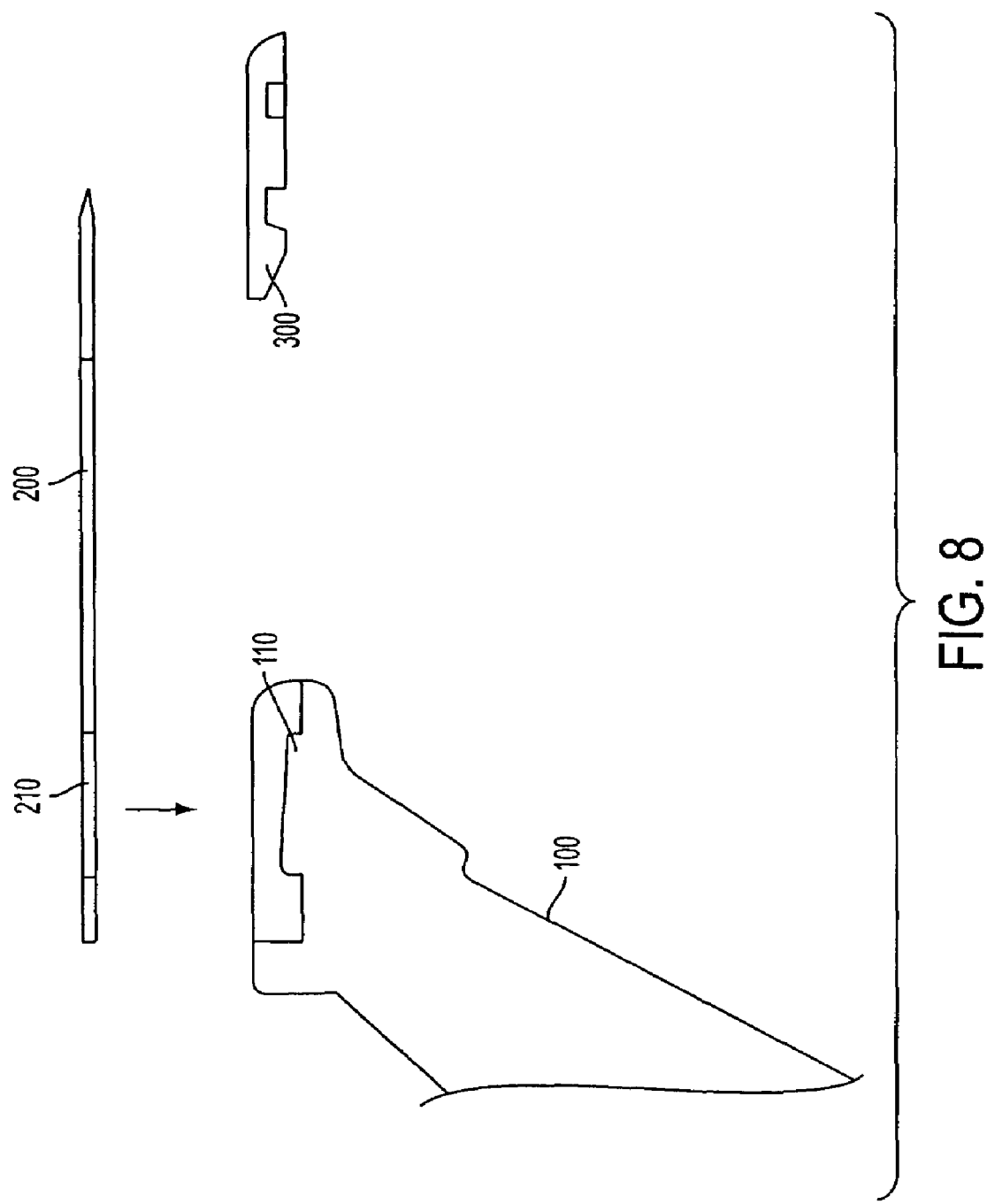
FIG. 8 is a partially exploded cross-sectional view of the handle base, blade and cap of FIG. 7.
Figure 9:
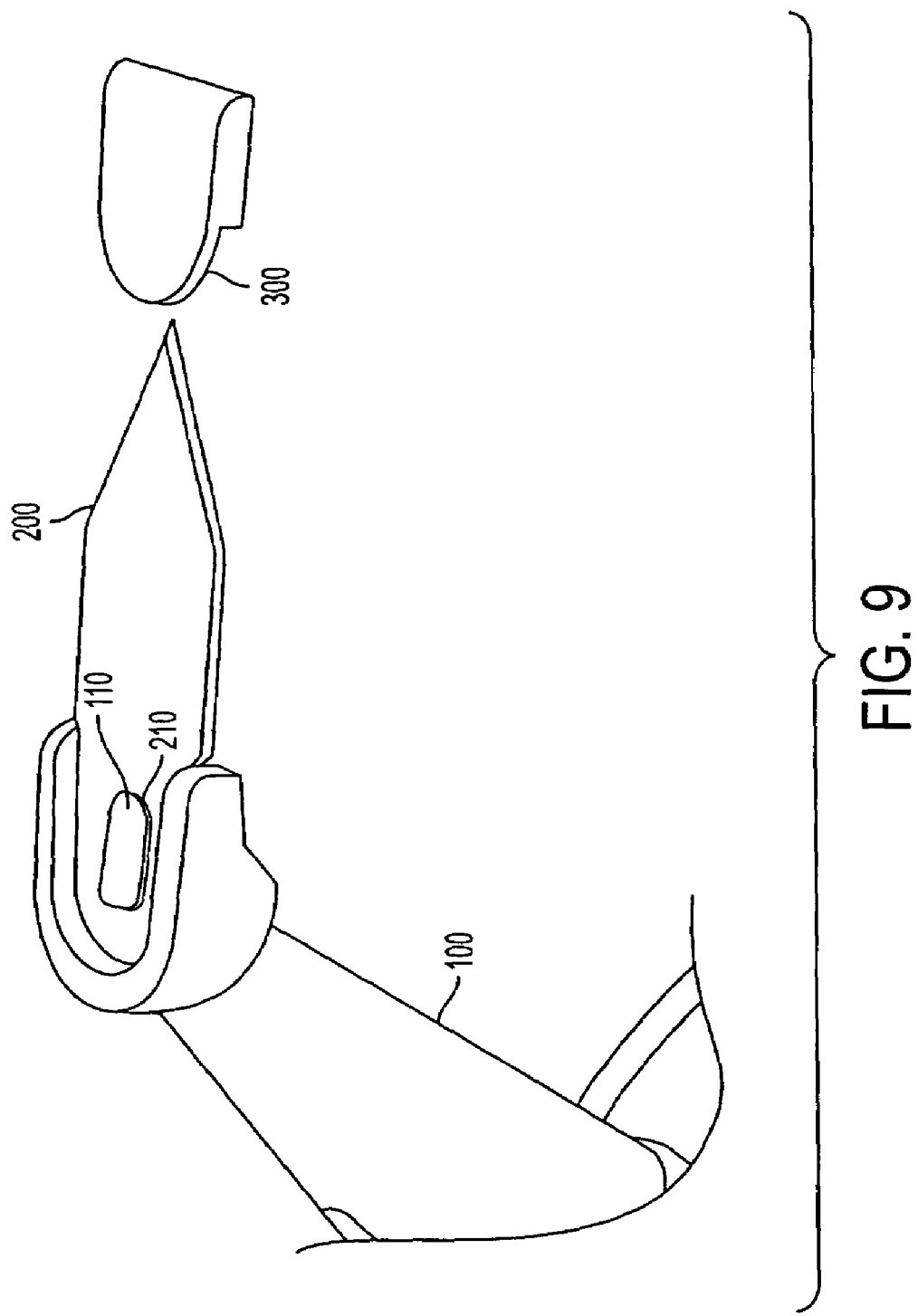
FIG. 9 is a partially exploded perspective view of the handle base with attached blade and removed cap of FIG. 7.
Figure 10:
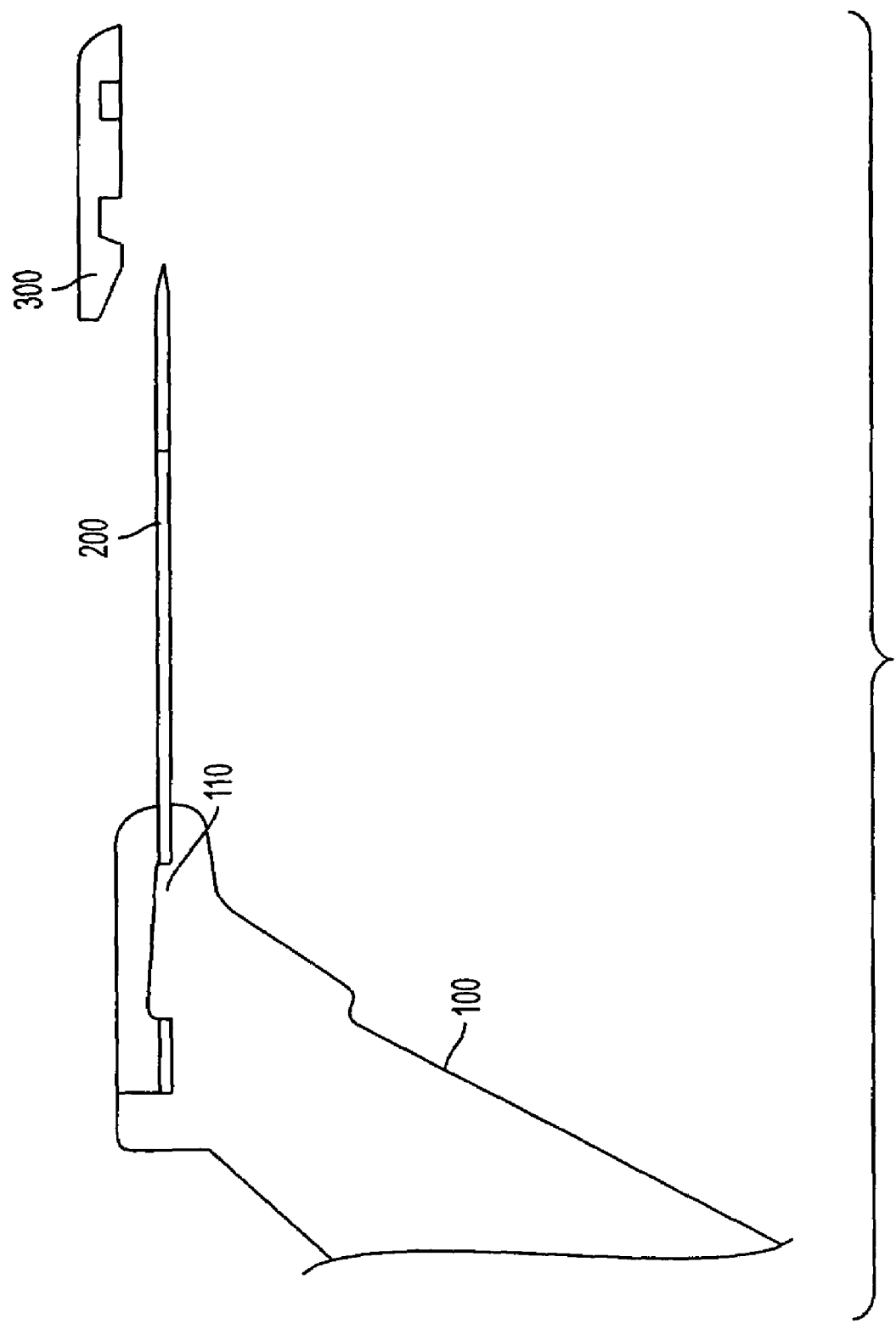
FIG. 10 is a partially exploded cross-sectional view of the handle base with attached blade and removed cap of FIG. 7.

The procedure with which the embodiment described above can be used to secure a blade to a handle is shown in FIGS. 7 through 14. FIGS. 7 through 14 illustrate the positioning and movement of handle 100, blade 200 and cap 300 to complete installation. In FIGS. 7 and 8 a blade 200 is first positioned above a handle base 100 with the blade opening 210 aligned with the center securing ramp 110. The blade 200 can then be securely lowered into the receiving port 102, allowing the center securing ramp 110 to extend through the blade opening 210, as shown in FIGS. 9 and 10. The cap 300 is then positioned parallel to the exposed blade surface and aligned to mate with the receiving port 102.

Figure 11:
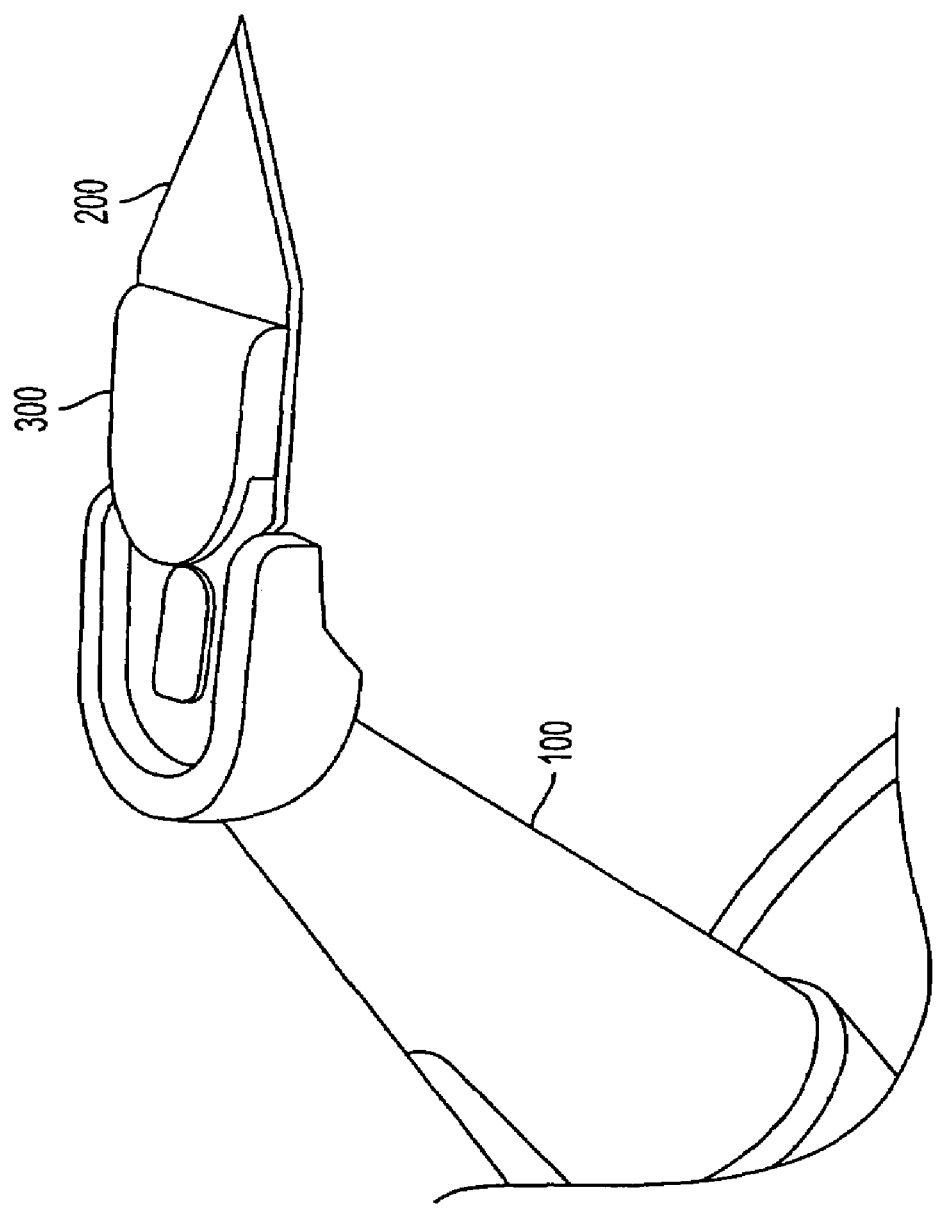
FIG. 11 is a partially exploded perspective view of the handle base with attached blade and removed cap in an aligned position of FIG. 7.
Figure 12:
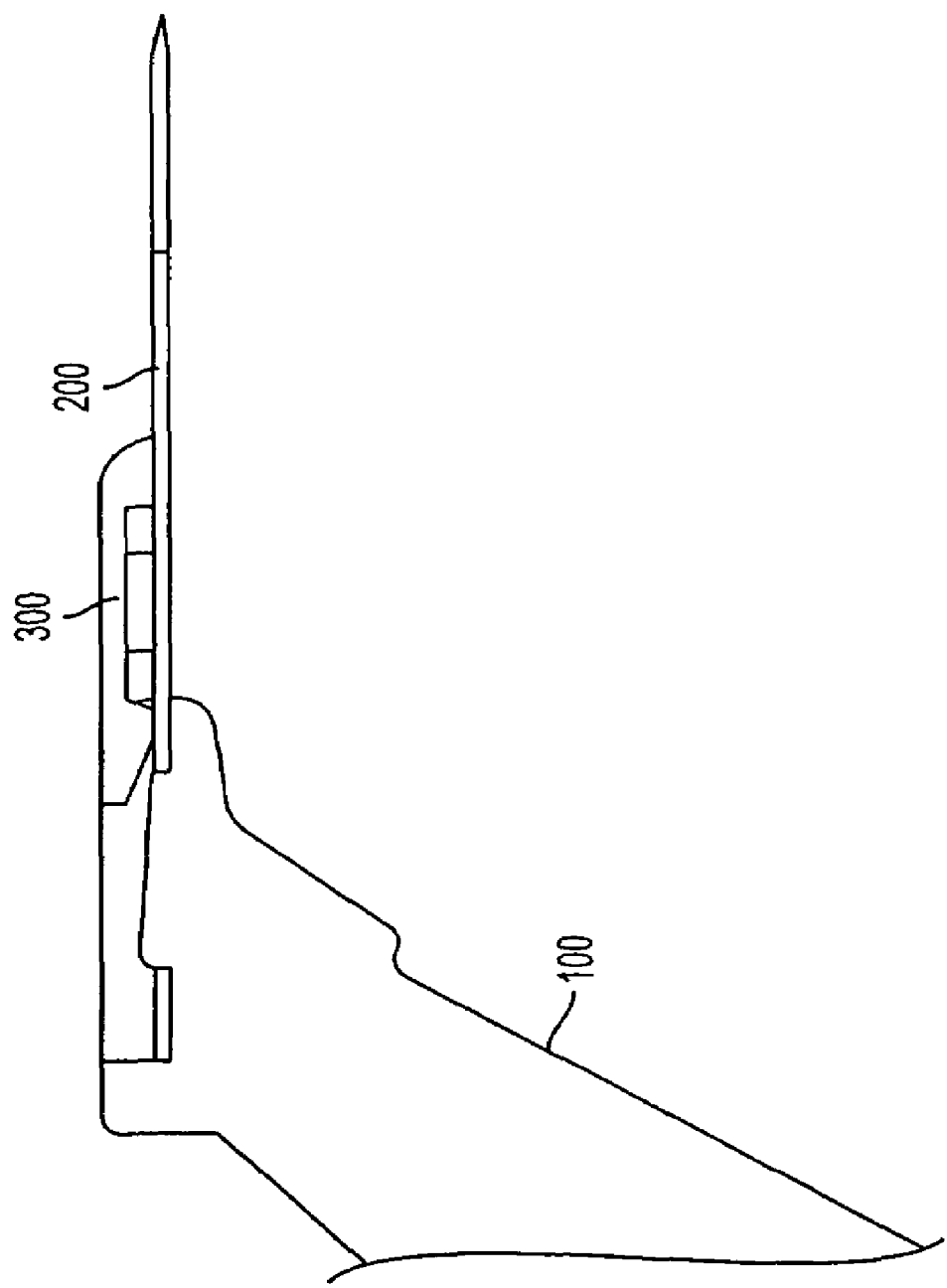
FIG. 12 is a partially exploded cross-sectional view of the handle base with attached blade and removed cap in an aligned position of FIG. 7.
Figure 13:
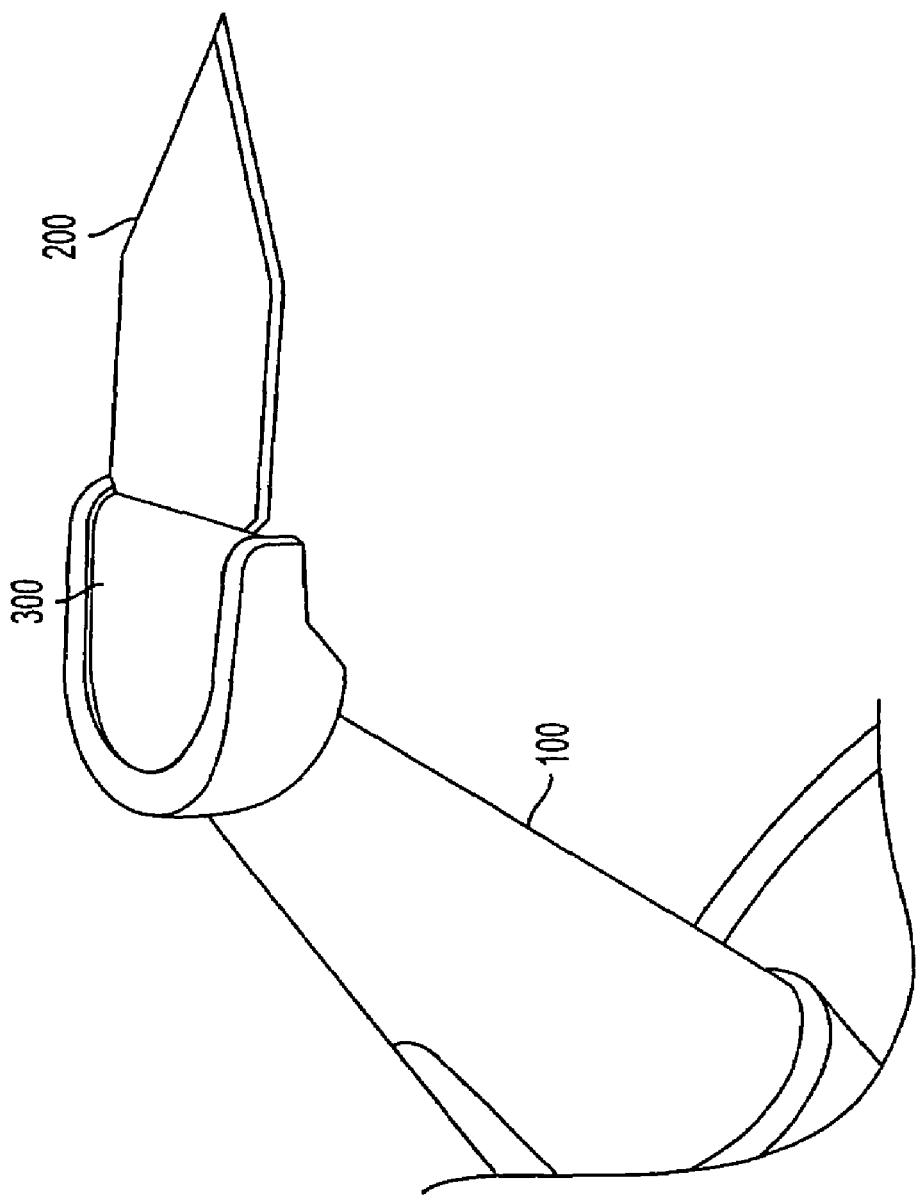
FIG. 13 is a perspective view of the handle base with attached blade and cap of FIG. 7.
Figure 14:
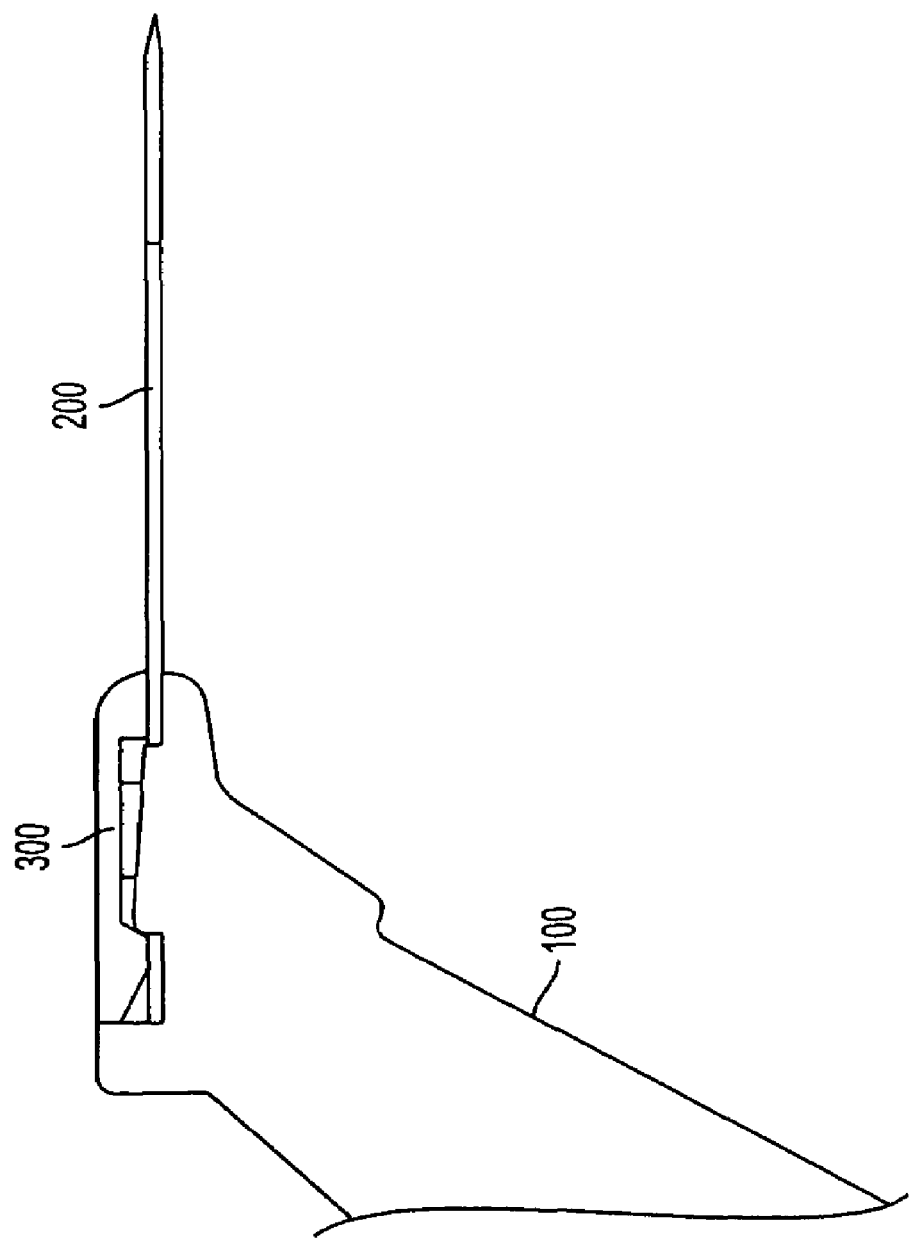
FIG. 14 is a cross-sectional view of the handle base with attached blade and cap of FIG. 7.

As shown in FIGS. 11 and 12, the cap 300 can then be disposed tightly against the exposed blade surface to allow a slidable movement of the cap along the parallel surface of the blade and into the receiving port 102, thereby allowing the dovetailed configuration of the receiving port sides 104 and 106 to slidably engage corresponding sides 304 and 306 of the cap 300. As the slidable engagement between cap 300 and base handle 100 occurs, the securing ramps 110 and 310 engage, as described above, until the cap is locked into a flush position as shown in FIGS. 13 and 14, thereby securing the blade 200 to the base handle 100.

Returning to FIG. 4, correct positioning of the blade 200 results from constructing the flat surface of the receiving port 102 at a desirable angle relative to the handle base centerline. As shown in FIG. 4, this angle is about 45 degrees, however, this angle can be increased or decreased as required by the application without altering the embodiment as described above.

Figure 15:
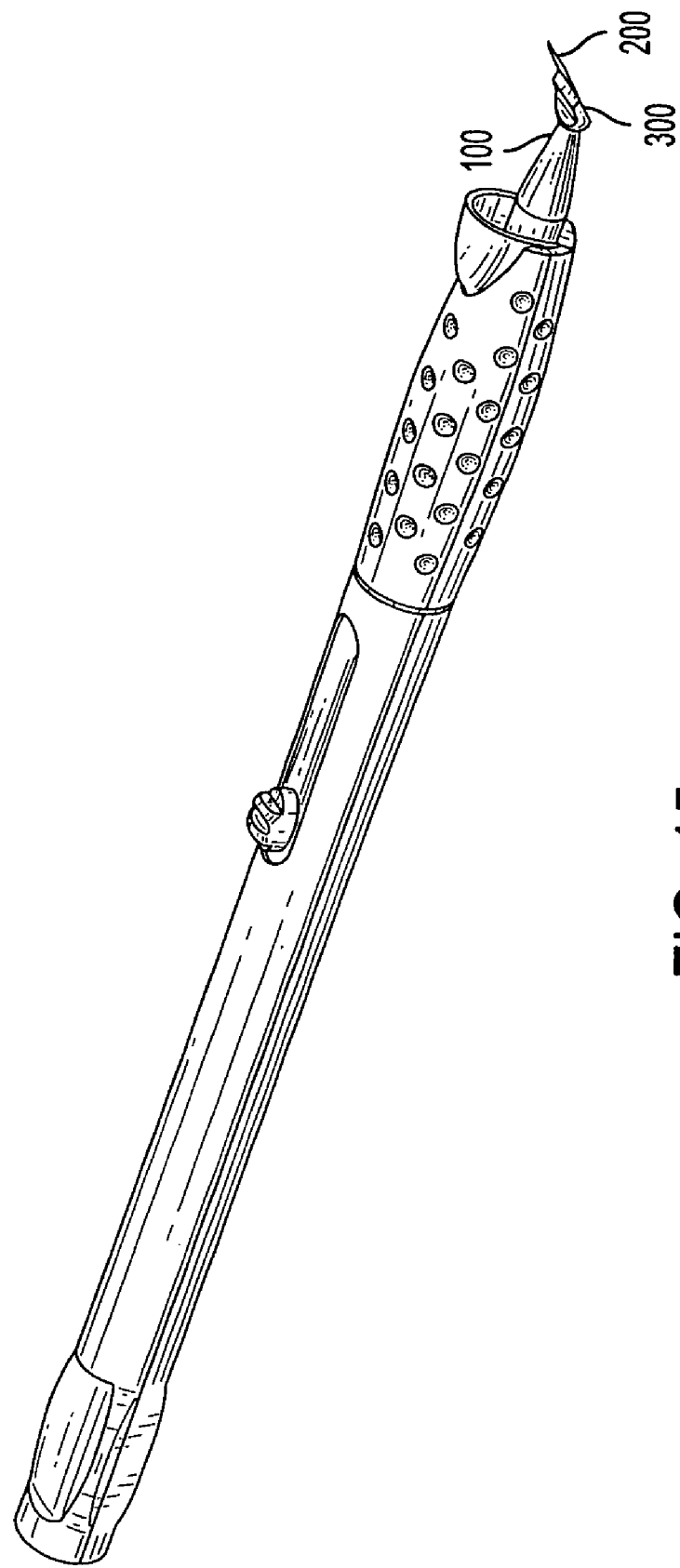
FIG. 15 is a perspective view of an example of a handle base with an attached blade and cap of FIG. 7 as found at the distal end of a surgical knife.

As shown in FIG. 15, the embodiment of the present invention can be used with a number of surgical knife safety handles and gives the user better control and allows easier blade orientation during use. In FIG. 15, the handle includes a handle base 100 as described above to fixedly secure the blade 200 to the distal end of the handle. In the example shown in FIG. 15, the handle base 100 is molded as an integral extension of the handle distal end and has a generally circular cross-section area at a point of attachment and is tapered slightly to a reduced cross-section area at a point of attachment to the blade. Additional details of a surgical knife safety handle are further discussed in a U.S. Patent Application of Michael J. Morawski et al., Ser. No. 10/828, 501, filed Apr. 21, 2004, in a U.S. patent application of Michael J. Morawski et al., Ser. No. 10/420,614, filed Apr. 22, 2003, entitled "Surgical Knife Safety Handle", and in a U.S. design patent application of Michael J. Morawski et al., Ser. No. 29/177,716, filed Mar. 17, 2003, entitled "Surgical Knife Safety Handle", the entire content of each of said applications being incorporated herein by reference.

The system and method of the embodiment described above is more advantageous than traditional blade attachment methods such as gluing. The use of glue such as epoxies is typically messy and labor intensive, and can often result in an unpredictable bond. Such compounds also typically require a curing cycle via an oven or UV light source. In contrast, the embodiment of the present invention described above can provide a rapid, secure and permanent bond without a need for a curing period or assisting device. Furthermore, the embodiment provides a tactile and audible feedback through the snap action of the cap and blade to provide the assembler feedback that the assembly is properly locked in place.

Although the present invention has been described with reference to an exemplary embodiment thereof, those skilled in the art will readily appreciate that many modifications are possible in the exemplary embodiment without materially departing from the novel teachings and advantages of this invention. Accordingly, all such modifications are intended to be included within the scope of this invention as defined in the following claims and equivalents thereof.

What is claimed is:

1. A blade securing system for attaching a blade to a handle base, comprising:
   a cap, comprising a flat top surface, a bottom surface and first, second, third, and fourth sides, wherein at least one of said first, second, third and fourth sides extends between said top and bottom surface at an angle;
   a handle base, having a receiving port comprising a bottom surface and first, second, and third sides, wherein at least one of said first, second and third sides extends from said bottom surface at an angle, said receiving port further comprising an open fourth side, and an open top side to receive a blade, said receiving port adapted to slidably engage said cap;
   a blade, having at least one opening and having a contoured end, adapted to fit within said receiving port, said contoured end secured to said handle base by said slidable engagement between said receiving port and said cap; and
   a center securing ramp disposed on said bottom surface of said receiving port and a second securing ramp disposed on said bottom surface of said cap, wherein said center securing ramp and said second securing ramp are positioned to lock in contact with each other by said slidable engagement between said receiving port and said cap, wherein:
   said center securing ramp is disposed on said bottom surface of said receiving port, said center securing ramp comprising a first incline and a rear surface;
   said at least one opening of said blade is configured to securely fit about said center securing ramp of said receiving port;
   said second securing ramp is disposed on said bottom surface of said cap, said second securing ramp comprising a second incline; and
   said slidable engagement between said receiving port and said cap engages said center securing ramp with said second securing ramp and disposes said second securing ramp between said rear surface of said center securing ramp and said third wall of said receiving port.

2. A blade securing system for attaching a blade to a handle base, comprising:
   a cap, comprising a flat top surface, a bottom surface and a continuous wall about said cap, said continuous wall having first, second, third, and fourth side portions, wherein at least one of said first, second, third and fourth side portions extends between said top and bottom surface at an angle;
   a handle base, having a receiving port comprising a bottom surface and a continuous wall about said receiving port, said continuous wall having first, second, and third side portions, wherein at least one of said first, second and third side portions extends from said bottom surface at an angle, said receiving port further comprising an open fourth side, and an open top side to receive a blade, said receiving port adapted to slidably engage said cap; and
   a center securing ramp disposed on said bottom surface of said receiving port and a second securing ramp disposed on said bottom surface of said cap, wherein said center securing ramp and said second securing ramp are positioned to lock in contact with each other by said slidable engagement between said receiving port and said cap, wherein:
   said center securing ramp is disposed on said bottom surface of said receiving port, said center securing ramp comprising a first incline and a rear surface;
   said second securing ramp is disposed on said bottom surface of said cap, said second securing ramp comprising a second incline; and
   said slidable engagement between said receiving port and said cap engages said center securing ramp with said second securing ramp and disposes said second securing ramp between said rear surface of said center securing ramp and said third wall of said receiving port.

3. A blade securing system for attaching a blade to a handle base, comprising:
   a cap, comprising a flat top surface, a bottom surface and first, second, third, and fourth sides, wherein at least one of said first, second, third and fourth sides extends between said top and bottom surface at an angle;
   a handle base, having a receiving port comprising a bottom surface and first, second, and third sides, wherein at least one of said first, second and third sides extends from said bottom surface at an angle, said receiving port further comprising an open fourth side, and an open top side to receive a blade, said receiving port adapted to slidably engage said cap;
   a blade, having at least one opening and having a contoured end, adapted to fit within said receiving port, said contoured end secured to said handle base by said slidable engagement between said receiving port and said cap; and
   a center securing ramp disposed on said bottom surface of said receiving port and a second securing ramp disposed on said bottom surface of said cap, wherein said center securing ramp and said second securing ramp are positioned to lock in contact with each other by said slidable engagement between said receiving port and said cap, wherein:
   said center securing ramp is disposed on said bottom surface of said receiving port, said center securing ramp comprising a first incline and a rear surface; and
   said cap further comprises a relief opening provided on said bottom surface of said cap to receive said center securing ramp on said bottom surface of said receiving port.

4. A blade securing system for attaching a blade to a handle base, comprising:
   a cap, comprising a flat top surface, a bottom surface and a continuous wall about said cap, said continuous wall having first, second, third, and fourth side portions, wherein at least one of said first, second, third and fourth side portions extends between said top and bottom surface at an angle;
   a handle base, having a receiving port comprising a bottom surface and a continuous wall about said receiving port, said continuous wall having first, second, and third side portions, wherein at least one of said first, second and third side portions extends from said bottom surface at an angle, said receiving port further comprising an open fourth side, and an open top side to receive a blade, said receiving port adapted to slidably engage said cap; and
   a center securing ramp disposed on said bottom surface of said receiving port and a second securing ramp disposed on said bottom surface of said cap, wherein said center securing ramp and said second securing ramp are positioned to lock in contact with each other by said slidable engagement between said receiving port and said cap, wherein:
   said center securing ramp is disposed on said bottom surface of said receiving port, said center securing ramp comprising a first incline and a rear surface; and said cap further comprises a relief opening provided on said bottom surface of said cap to receive said center securing ramp on said bottom surface of said receiving port.

5. A blade securing system for attaching a blade to a handle base, comprising:
   a cap, comprising a flat top surface, a bottom surface and first, second, third, and fourth sides, wherein at least one of said first, second, third and fourth sides extends between said top and bottom surface at an angle;
   a handle base, having a receiving port comprising a bottom surface and first, second, and third sides, wherein at least one of said first, second and third sides extends from said bottom surface at an angle, said receiving port further comprising an open fourth side, and an open top side to receive a blade, said receiving port adapted to slidably engage said cap;
   a blade, having at least one opening and having a contoured end, adapted to fit within said receiving port, said contoured end secured to said handle base by said slidable engagement between said receiving port and said cap; and
   a center securing ramp disposed on said bottom surface of said receiving port and a second securing ramp disposed on said bottom surface of said cap, wherein said center securing ramp and said second securing ramp are positioned to lock in contact with each other by said slidable engagement between said receiving port and said cap, wherein:
   said first and second sides of said receiving port are adapted to slidably engage said first and second sides of said cap, said slidable engagement comprising a dovetail connection between said handle base and said cap.

6. A blade securing system for attaching a blade to a handle base, comprising:
   a cap, comprising a flat top surface, a bottom surface and a continuous wall about said cap, said continuous wall having first, second, third, and fourth side portions, wherein at least one of said first, second, third and fourth side portions extends between said top and bottom surface at an angle;
   a handle base, having a receiving port comprising a bottom surface and a continuous wall about said receiving port, said continuous wall having first, second, and third side portions, wherein at least one of said first, second and third side portions extends from said bottom surface at an angle, said receiving port further comprising an open fourth side, and an open top side to receive a blade, said receiving port adapted to slidably engage said cap; and
   a center securing ramp disposed on said bottom surface of said receiving port and a second securing ramp disposed on said bottom surface of said cap, wherein said center securing ramp and said second securing ramp are positioned to lock in contact with each other by said slidable engagement between said receiving port and said cap, wherein:
   said first and second sides of said receiving port are adapted to slidably engage said first and second sides of said cap, said slidable engagement comprising a dovetail connection between said handle base and said cap.

7. A blade securing method for attaching a blade to a handle base, comprising:
   positioning a blade within a receiving port of a handle base, said receiving port comprising at least one tapered side and a center securing ramp;
   slidably engaging a cap with said receiving port, said cap comprising at least one tapered side and a bottom surface having a second securing ramp, wherein said slidable engagement mates said tapered side of said receiving port with said tapered side of said cap; and
   slidably engaging said center securing ramp of said receiving port with said second securing ramp of said cap, wherein said center securing ramp and said second securing ramp are positioned to lock in contact with each other by said slidable engagement and secure said cap and said blade within said receiving port, wherein:
   said slidable engagement between said tapered side of said receiving port and said tapered side of said cap comprises a dovetail connection between said handle base and said cap.

* * * * *